US012736445B2

(12) United States Patent
Arold et al.

(10) Patent No.: US 12,736,445 B2
(45) Date of Patent: Sep. 15, 2026

(54) METHOD AND DEVICE FOR PREPARING A GRINDING PATTERN FOR A METALLURGICAL SAMPLE

(71) Applicant: Robert Bosch GmbH, Stuttgart (DE)

(72) Inventors: Markus Arold, Frensdorf (DE); Axel Bormann, Bamberg (DE); Christoph Straubmeier, Bamberg (DE); Dennis Quest, Bamberg (DE)

(73) Assignee: Robert Bosch GmbH, Stuttgart (DE)

( * ) Notice: Subject to any disclaimer, the term of this patent is extended or adjusted under 35 U.S.C. 154(b) by 273 days.

(21) Appl. No.: 18/700,079

(22) PCT Filed: Sep. 26, 2022

(86) PCT No.: PCT/EP2022/076676
§ 371 (c)(1),
(2) Date: Apr. 10, 2024

(87) PCT Pub. No.: WO2023/078614
PCT Pub. Date: May 11, 2023

(65) Prior Publication Data

US 2024/0344941 A1 Oct. 17, 2024

(30) Foreign Application Priority Data

Nov. 3, 2021 (DE) ..................... 10 2021 212 385.6

(51) Int. Cl.
*G01N 1/32* (2006.01)
*G01N 1/28* (2006.01)
(Continued)

(52) U.S. Cl.
CPC ............... *G01N 1/286* (2013.01); *G01N 1/44* (2013.01); *G01N 33/207* (2019.01); *G01N 2001/2866* (2013.01)

(58) Field of Classification Search
None
See application file for complete search history.

(56) References Cited

U.S. PATENT DOCUMENTS 11,471,980 B2 * 10/2022 Qiao .................... B23K 26/082
2006/0244955 A1 * 11/2006 Schramm ........... G01N 21/9501 356/237.2

(Continued)

FOREIGN PATENT DOCUMENTS

WO 2013117667 A1 8/2013

OTHER PUBLICATIONS

Translation of International Search Report for Application No. PCT/EP2022/076676 dated Dec. 16, 2022 (2 pages).

*Primary Examiner* — Alexander A Mercado
(74) *Attorney, Agent, or Firm* — Michael Best & Friedrich LLP

(57) ABSTRACT

The invention relates to a method and a device for preparing a grinding pattern for a metallurgical sample (1), wherein, after preparing the sample (1), a thermal contrasting of the surface is carried out by laser equipment, wherein, using a USP laser (2), at least the following processing steps are carried out:

cleaning (R) the surface of the sample (1) with an ablation depth of between 1 to 50 μm to reveal joining gap structures (300);

contrasting (K) the cleaned surface of the sample (1) with an ablation depth between 0.5 to 20 μm to make joining structures (400) visible;

laser etching (A) the contrasted surface of the sample (1) via the ablation-free creation of a thermal annealing color structure (500) and/or surface oxidation.

15 Claims, 2 Drawing Sheets

(51) Int. Cl.

| | |
|---|---|
| ***G01N 1/44*** | (2006.01) |
| ***G01N 33/207*** | (2019.01) |

(56) References Cited

U.S. PATENT DOCUMENTS

| | | | | |
|---|---|---|---|---|
| 2013/0081882 | A1* | 4/2013 | Lin | G01N 1/32<br>175/428 |
| 2014/0130613 | A1* | 5/2014 | Adiga | G01N 1/06<br>73/864.41 |
| 2021/0053160 | A1* | 2/2021 | Qiao | B23K 26/402 |
| 2023/0003655 | A1* | 1/2023 | Lu | G01N 21/718 |
| 2023/0191544 | A1* | 6/2023 | Höll | G01N 1/36<br>29/428 |
| 2025/0322733 | A1* | 10/2025 | Swierkowski | G03B 21/00 |
| 2026/0045525 | A1* | 2/2026 | Laube | C25B 1/04 |

* cited by examiner 1
2
3
4
5
6
7
8
9
10
11
12
x
y
z

METHOD AND DEVICE FOR PREPARING A GRINDING PATTERN FOR A METALLURGICAL SAMPLE

BACKGROUND

The present invention relates to a method for preparing a grinding pattern for a metallurgical sample, wherein after preparing the sample, a thermal contrasting of the surface is carried out by laser equipment. In addition, the invention also relates to a device for carrying out this method for preparing a grinding pattern.

The application area of the invention primarily extends to the quality testing of metallic workpieces, in particular in the region of the weld seams connecting the components. For the assessment of metal weld connections, the metallurgical grinding patterns of interest here are usually produced, which can be materialographically analyzed, for example, by means of a light microscope in a known manner. Weld seams, structural and grain boundaries, heat influence zones, welding depths, joining widths, joining gaps and the like are visible in the grinding pattern.

According to the generally known prior art, such grinding patterns are so far prepared by embedding a sample of the workpiece in plastic, cutting the sample and performing several grinding processes up to and including polishing and etching to obtain a meaningful grinding pattern.

This is done using various tools in a time consuming process. Often, the desired quality of a grinding pattern, which allows a clear detection as well as statement about the aforementioned characteristics, cannot be achieved. Thus, undifferentiated dark surfaces can be created in the grinding pattern, which do not allow any distinction between the weld seam, heat influence zones, and the basic structure of the workpiece. On the other hand, excessive contrast differences in the grinding pattern can also make the evaluation more difficult. In addition, chemical etching agents, which require special treatment and are harmful to health, are normally used for the last preparation step of etching. Due to the machining steps of the surface that are used for the conventional grinding pattern preparation, narrow joining gaps can be added by ablated material and are therefore no longer discernible.

WO 2013/117667 A1 provides a generic method for preparing a grinding pattern, which is based on laser etching instead of chemical etching. In this case, the surface of a metallurgical sample to be analyzed materialographically is partially subjected to a polishing process and then processed with at least one laser beam such that due to the thermal expansion of the grains of the processed sample surface, a microstructure is obtained, which is materialographically analyzed. The processing of the sample surface is preferably carried out with at least one laser beam under a protective gas atmosphere. As part of the laser etching, the sample surface is processed in a partial grid-like manner. The laser beam of a fiber laser, laser-guided diode laser or carbon dioxide laser is used to apply a certain energy density to the sample surface, wherein, depending on the coefficient of thermal expansion of the sample material, the grains of the processed surface expand and, at the same time, evaporation occurs at the grain boundaries due to the greater defect density in the crystal lattice, therefore material is removed. The processing of the sample surface is preferably carried out under atmospheric conditions or oxygen addition. The joint is thereby visibly enhanced, wherein the contrast enhancement takes place up to the oxidation limit.

Nevertheless, in the context of this non-chemical grinding pattern preparation, a mechanical processing of the surface prior to laser etching takes place by polishing, which is accomplished by using various grinding and polishing devices with decreasing grain size. In addition, cleaning of the polished surface by an ultrasonic bath is proposed as part of the grinding pattern preparation. Overall, therefore a number of processing machines and tools are used, which results in a laborious and time-consuming grinding pattern preparation of metallurgical samples.

SUMMARY

The object of the present invention is therefore to create a method as well as a device for the grinding pattern preparation of a metallurgical sample, which ensures simple and fast grinding pattern preparation in terms of production and technology.

The task is solved in a process-related manner by the disclosure. The secondary device specifies a suitable device for carrying out the multi-step method according to the invention.

The invention includes the methodological teaching that for the grinding pattern preparation of a metallurgical sample, in which thermal contrasting of the surface is carried out by laser equipment instead of chemical etching after preparing the sample, the entire grinding pattern preparation including processing is carried out with an ultra-short pulse (USP) laser, which performs at least the following processing steps:

- cleaning R the surface of the sample having an ablation depth of between 1 to 50 μm to reveal joining gap structures,
- contrasting K the cleaned surface of the sample with an ablation depth of between 0.5 to 20 μm to make joining structures visible,
- laser etching A the contrasted surface of the sample by ablation-free creation of a thermal annealing color structure and/or surface oxidation.

Here a thermal annealing color structure is created by heating the sample until annealing colors become visible on the surface. Such annealing colors, also known as tarnish colors, are iridescent colorings of a fabric on the surface that arise from interference on thin layers. They are found primarily in metals but also on minerals. This interference is very similar to that in oil spots on puddles or in lamellae of soap bubbles, and allows conclusions to be drawn about the material properties.

A joining structure is understood to refer to the association of crystallites and grains in a metal. Since crystallization often begins at many points of the melt simultaneously, a piece of metal consists of a plurality of individual crystals that have grown together. Structural features are, for example, the grain size, the grain shape as well as different phases or segregations. The formation of the joint is determined by many factors such as alloying element content, manufacturing conditions or processing conditions. Corresponding material properties can be read and tested from this.

A joining gap structure is understood to refer to arrangements of joining gaps formed between adjacent components. A joining gap can be interrupted by a weld seam connecting the components.

The advantage of the solution according to the invention is in particular that not only chemical etching is replaced by laser etching, but also the previous sample processing is performed by laser technology, which in the context of the invention makes it possible to use a single USP laser, which is only operated with correspondingly adjusted parameters for the different processing steps.

For example, if the surface of the metallurgical sample is rough-sawn, then cleaning R can optionally be preceded by smoothing G of the surface to sufficiently level it, i.e., remove the saw marks. The optional smoothing G thus evens out imperfections as they can be produced in the case of rough-sawn cuts and provides a basis for the subsequent treatment process. Conventional cascade grinding steps as well as a final polishing can thereby be omitted. The parameters for the USP laser are selected for smoothing G such that cutting grooves, imperfections, and the like are completely removed, which is preferably performed by multiple passes with the laser beam at an ablation depth of between 1 to 150 μm, preferably 20 to 150 μm, depending on the pre-processing state of the sample. To level a rough surface by smoothing, sufficient material removal is required. If the sample is already pre-ground and polished, a single pass with the USP laser is usually sufficient to sufficiently smooth the surface. Since this cannot be completely free of ablation, a lower limit of 1 μm ablation depth applies for smoothing. If no homogeneous smoothed surface is achieved after 150 μm, the sample may need to be mechanically pre-treated, for example by grinding.

The subsequent cleaning R provides the option of revealing the joining gap added by the pre-treatment. For the method step of cleaning R, the laser parameters are selected such that the material removal just visibly reveals the joining gap structures, which could be added by the previous processing. For this purpose, multiple passing with the laser beam with an ablation depth of between 1 to 50 μm is also carried out. In order to remove residue from joining gaps, the ablation process must be run at a certain power density. This also always causes some material to be lost on the sample itself. Ablation depths of more than 50 μm therefore make no sense as the upper range limit, since the sample is generally already level and pretreated. For cleaning, a larger ablation depth is selected in contrast to smoothing for the same sample.

The subsequent contrasting K additionally allows a visualization of, for example, weld seam mixing, contrast reductions of the heat influence zone, diffuse contrasting in the form of mattings and the like. This further improves the visibility of weld seams. This specific contrasting K is done with laser parameters set to produce a homogeneous matte surface, which is achieved by single or multiple passing of the laser beam with an ablation depth of between 0.5 to 20 μm. For the contrasting, only a single line-by-line passing over the surface with the USP laser is usually necessary, with which the specified lower limit value of the ablation depth of 0.5 μm can be realized. In an n-fold pass in preferably different hatching directions, the ablation depth increases with the factor n. To a lesser extent, this of course is also alternatively or additionally variable via the laser power, the fluence. As with smoothing and cleaning, the upper limit value serves as a differentiating feature from the other method steps.

Final laser etching A allows for thermal sample preparation without liquid etching agents by oxidizing contaminants at grain/melt boundaries for visualization of finer surface structures. This is done under an air or oxygen atmosphere as a process gas, wherein the laser beam is defocused and the feed is preferably performed in a meandering manner in lines. No material removal takes place here. Rather, heat is specifically introduced into the surface of the metallurgical sample and the surface is oxidized in a controlled manner by means of process gas. Since impurities at grain boundaries, melt zone transitions and the like react chemically stronger on the surface, as well as a microheat build-up arises, the structure or the weld seam becomes visible.

The solution according to the invention allows the use of the same laser tool for laser etching, as has also been used for the previous sample preparation, which represents a considerable simplification in terms of process technology and allows for a quick grinding pattern preparation of the metallurgical sample by eliminating tool changes. In addition, there is the advantage that the solution according to the invention is also suitable for use on already existing grindings, even only polished, ground or even only separated sample surfaces. Thus, the optional smoothing G is generally only provided for the elimination of rough surfaces, which ensures a flexible application depending on the sample condition. The conventional preparation process by grinding, polishing and etching is replaced by this or at least significantly simplified. Because in principle, the solution according to the invention can be applied as needed at different stages of the grinding pattern preparation—from rough sawn to completely contrasted—in order to create a meaningful metallurgical grinding pattern.

The parameters for the individual machining steps typically have to be developed and tested individually for each welded joint due to different circumstances, such as materials of the joining partners, thermal conductivity, size, pre-treatment state. In principle, a minimum to maximum number of passes is carried out until the stop criterion of a sufficiently well-smoothed, cleaned or contrasted surface is achieved for each processing step. This is determined by subjective visual inspection of the sample surface after each processing step.

For smoothing, a score-free clean surface is considered a stop criterion. The area of the weld seam and adjacent areas relevant for the assessment of the weld depth or weld width are flat and preferably free of pre-treatment, i.e., traces of a pre-treatment are no longer visible. This can be assessed by means of a visual inspection without aids.

For cleaning, the test is carried out under a microscope. For example, the stop criterion is when the joining gap is revealed. The joining gap is clearly visible and burrs or grinding residues are completely removed.

For contrasting, the stop criterion is checked to determine whether there is a visibility of the weld seam or a sufficient contrast with the basic structure for clearly determining the position of the weld seam.

Accordingly, success is generally visually checked manually and, except for smoothing, with the aid of a reflected-light microscope. In addition, an automatic assessment by pattern comparison or the like is also conceivable.

Preferably, the USP laser for laser etching A is operated at a constant wavelength λ in the range between 1020 nanometers (nm) to 1040 nm, preferably 1030 nm with a tolerance of usually +/−3 nm, combined with a pulse width $t_P$ of ≤10 picoseconds (ps). In contrast to the prior art, in which a cw-pulsed or ns-pulsed laser is described for laser etching, the aforementioned specified operating parameters can be achieved with the USP laser employed in the context of the present invention.

According to a further measure improving the invention, it is proposed that at least the material-removing steps of cleaning R and contrasting K be carried out in accordance with a uniformly linear ablation pattern. This ablation pattern can be generated by the scanning system of the device. In this case, the pattern is applied at an angle of preferably 45° with at least six hatching directions, preferably eight hatching directions, per ablation. Depending on the requirements, the operating parameters including the number of repeats, hatching distance, laser power, focus position, scanning speed, inert gas, etc. are varied in order to obtain a defined depth, homogeneous ablation for cleaning R and contrasting K as well as for optional smoothing G.

The above described multi-step method for preparing a grinding pattern with a USP laser can be implemented with a device, which, in addition to the USP laser for generating a laser beam, also comprises a beam deflection unit, a so-called scan head, to move and focus the laser beam along the surface of the metallurgical sample, a sample clamping unit for positioning the metallurgical sample relative to the beam deflection unit and an electronic control unit for coordinated control of at least the aforementioned units of the device in accordance with method step G; R; K; A.

The coordinated control of the units takes place in such a way that work is always performed in the defocused area. Steps G; R; K differ in that when smoothing, more passes than when cleaning are needed than when contrasting. Coordinated control is understood here to mean programming of the ablation geometry, which is defined by parameters such as shape, fill pattern of the shape (ablation pattern in different hatching directions), power, processing speed, slip velocity, hatching angle, repetitions, defocusing, jump/start and stop characteristics (for example LaserOnDelay, LaserOffDelay, Skywriting).

The fluence during smoothing should be 0.6 J/cm2 with a tolerance of +/−0.1 J/cm2 in order to obtain a good machining result, for example with about 6 watts of laser power, therefore to avoid material foaming or conical formation due to defects. For contrasting and cleaning, this can be deviated from and comparatively less laser power can be output, for example 4 to 5 Watts are already sufficient for this depending on the device, which leads to a correspondingly reduced fluence.

Etching specifically involves even stronger defocusing in comparison to the aforementioned method steps in order to obtain a larger spot diameter on the component surface. The aim is to generate local heating up to the usual material-dependent annealing temperature range in order to make the grain boundaries visible by means of the annealing colors. The laser thus no longer has an ablative effect, but only a thermal one.

The coordinated control of the various units of the device includes placing the sample in the sample clamping unit and a method of the axes of the sample clamping unit, such that the focus position of the laser beam is aligned with the component surface, preferably defocused −1.7 mm below the component surface for sample preparation as part of step G, R, K. With the beam deflection unit, a defined deflection of the laser beam for pattern generation is performed according to a scanning program.

For example, to process a square of 4×4 mm edge length on the sample surface, a laser power of 6 W at 400 kHz pulse sequence frequency is generated using the USP laser. The paths of the ablation pattern are traversed at a feed rate of 2 m/s. The line spacing of the ablation pattern is 0.02 mm. First, only one direction is machined. A direction number of 8 results in a so-called hash angle of 45°. In other words, the generated line pattern is carried out 8 times in total and rotated 45° between each step to achieve homogeneous ablation without preferential direction.

These 8 steps per hatching plane are repeated until the ablation depth specified according to the scanning program is achieved. Then the scanning program is stopped and the sample is moved to the removal position to visually check the result of the machining step manually. If the result is not yet satisfactory, processing is continued.

In addition, in the device between the USP laser and the beam deflection unit, a so-called focus shifter, for example a Varioscan unit (varioSCAN® from Scanlab) can be arranged. The focus shifter includes focusing optics which allows for highly dynamic and extremely precise positioning of the laser focus along the optical Z-axis. This allows XY laser units to be easily expanded to 3D beam deflection systems. The laser focus can be guided along the contour of the workpiece to be processed. For this purpose, the focusing optics can be moved by a motor in order to also continuously adjust the working distance and the spot size for defocusing.

Furthermore, a beam width unit for increasing or decreasing the laser beam cross section can also be arranged between the USP laser and the focus shifter. A collimated laser beam is recorded and enlarged or reduced in cross section.

According to a further measure that improves the invention, it is proposed that the sample clamping unit be equipped with CNC kinematics in order to spatially position the sample to be processed in relation to the beam deflection unit arranged relatively stationary for this purpose. This ensures that the top of the sample is in the focus of the laser beam.

However, it is also conceivable that a manual set-up is performed.

The ablation depth is varied in principle by the number of passes, wherein the ablation depth per pass can be described as a function of laser power and beam diameter at the processing location, scan speed, material, line spacing of the hash pattern, angle of the hash patterns and number of hash patterns. The resulting ablation depth of tenths of a micron to a few microns is then substantially constant as a process result over the scanned range.

BRIEF DESCRIPTION OF THE DRAWINGS

Further measures improving the invention are described in greater detail below on the basis of the figures, together with the description of a preferred embodiment example of the invention. The figures show.

DETAILED DESCRIPTION

Figure 1:
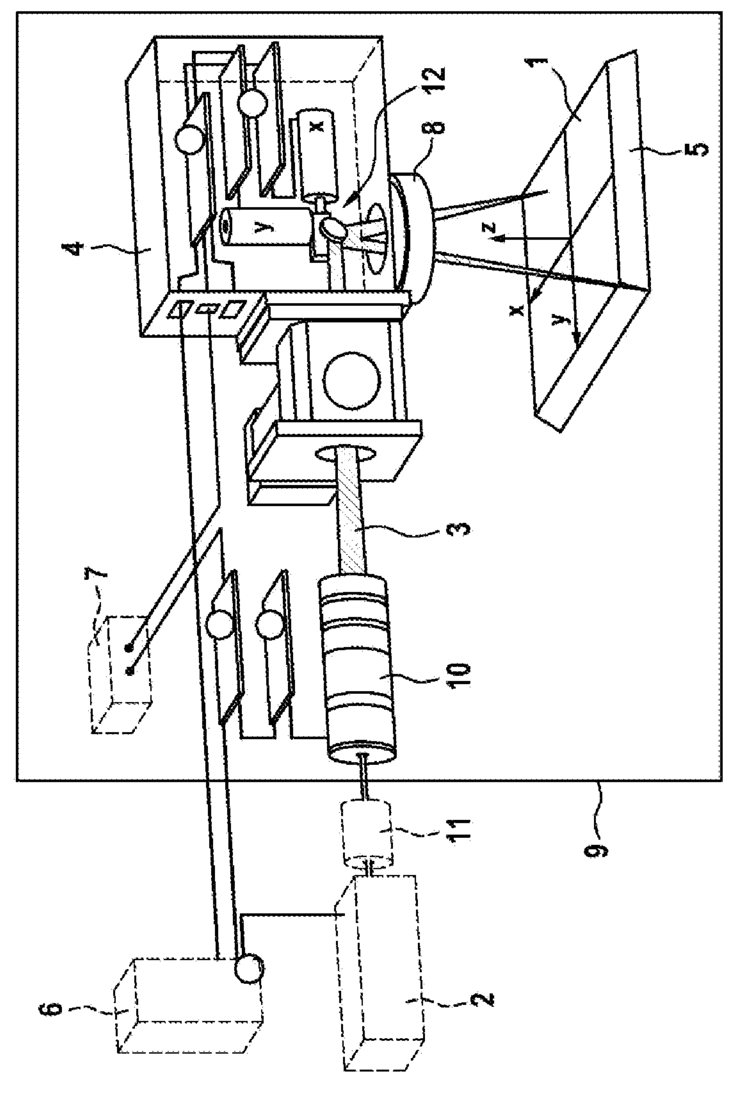
FIG. 1 a schematic illustration of a device for preparing a grinding pattern for a metallurgical sample by USP laser, FIG. 2 a flow chart of method steps G; R; K; A performed with the device according to FIG. 1, and FIG. 3 a grinding pattern for a metallurgical sample as a result of the machining steps according to the invention.

According to FIG. 1, a device for preparing a grinding pattern of a metallurgical sample 1 consists essentially of a USP laser 2, which is operated with a pulse width $t_p$ of ≤10 ps at a wavelength Λ of 1030 nm and serves to generate a laser beam 3, which is directed via a beam deflection unit 4 for movement and focusing of the laser beam 3 relative to the surface of sample 1. The sample 1 is positioned relative to the beam deflection unit 4 by means of a sample clamping unit 5 and is equipped with CNC kinematics—not shown further here—in order to position the sample 1 to be processed spatially according to the illustrated axes x, y, z in comparison to the relatively stationary arranged beam deflection unit 4, which is designed in this respect according to the type of a laser head.

An electronic control unit 6, which is in communicative communication with the units or components of the system, serves for the coordinated control of the components or units of the device. The power is supplied via a power supply unit 7. The device forms a 2(3)D-Galvano scanning system equipped with an f-theta lens 8 for focusing the laser beam 3. The method according to the invention, which is to be carried out with the device and which is sometimes carried out with multiple steps, represents a laser class 4 process, which is accommodated within a closed housing 9 and is thus encapsulated in a laser-tight manner. Outside of the closed housing 9, laser class 1 prevails.

Furthermore, a focus shifter 10 for positioning the laser focus along the optical Z-axis of the laser beam 3 is arranged between the USP laser 2 and the beam deflection unit 4. Between the USP laser 2 and the focus shifter 10 there is an additional beam scale unit 11 for increasing or decreasing the laser beam cross section before it enters the area of the closed housing 9.

The beam deflection unit 4 comprises a dual-axis mirror system 12 for controlling the laser beam 3 along the surface of the sample 1 to be processed according to an ablation pattern predetermined by the electronic control unit 6.

Figure 2:
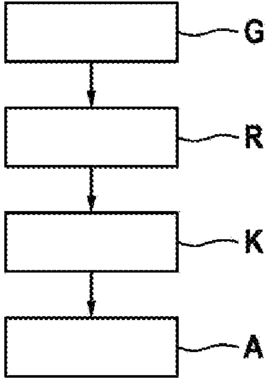

According to FIG. 2, with the aforementioned device, grinding pattern preparation for the metallurgical sample 1 can be carried out, which in this embodiment example assumes a sample 1 with cutting grooves, i.e., a very rough surface. In a first step, a smoothing G of the surface of the sample 1 for leveling the surface is carried out so that the cutting grooves are completely removed by passing the surface several times at an ablation depth of 20 to 150 μm.

After this leveling, in a second step, a cleaning R of the surface of the sample 1 is carried out, which serves to reveal joining gap structures on the surface of the sample 1. For this purpose, multiple passing with the laser beam 3 takes place with an ablation depth of between 1 to 50 μm, until any joining gap structures that are present become visible.

In a third step, contrasting K of the cleaned surface of the sample 1 is performed to visualize joining structures. This also is also done by multiple passing with the laser beam 3 with an ablation depth of between 0.5 to 20 μm. A flat, homogeneously matte surface is thereby produced.

In a fourth and final step, laser etching A of the contrasted surface of the sample 1 is performed by the laser beam 3 under air or oxygen as a process gas, wherein the laser beam is defocused and guided in a meandering manner in lines across the surface of the sample 1. This selectively introduces heat into the sample 1 and by means of process gas oxidizes the surface in a controlled manner to make the microstructure or a contained weld seam visible. Subsequently, a materialographical evaluation of the prepared grinding pattern is carried out in a known manner, for example with a light microscope.

Figure 3:
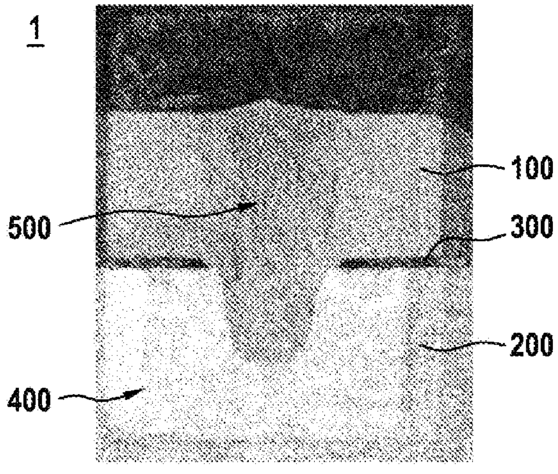

FIG. 3 shows an exemplary grinding pattern in which components 100 and 200 are welded together and the intervening joining gap 300 are visible, which protrudes in high contrast as a result of cleaning R. In addition, contrasting K renders joining structures 400 visible on the sample surface and laser etching A results in thermal annealing colors 500 projecting visually in the weld seam region.

The invention is not limited to the preferred embodiment example described above. Rather, it is also conceivable to make modifications to this, which are included in the scope of protection of the following claims. For example, it is also possible for the smoothing G of the surface of a sample to be omitted if the sample is already sufficiently level in the initial situation.

The invention claimed is:

1. A method for preparing a grinding pattern for a metallurgical sample (1) using an ultra-short pulse (USP) laser, the method comprising:

cleaning (R), using the USP laser, a surface of the sample (1) with an ablation depth of between 1 to 50 μm to reveal joining gap structures (300);

contrasting (K), using the USP laser, the surface of the sample (1) with an ablation depth of between 0.5 to 20 μm to make joining structures (400) visible after cleaning (R); and laser etching (A), using the USP laser, the surface of the sample (1) via an ablation-free creation of a thermal annealing color structure (500) and/or surface oxidation after contrasting (K).

2. The method according to claim 1, further comprising smoothing (G), using the USP laser, the surface of the sample (1) with an ablation depth of between 20 to 150 μm for leveling surfaces before the cleaning (R).

3. The method according to claim 2, wherein at least material-removing steps of cleaning (R) and contrasting (K) are carried out in accordance with a uniformly linear ablation pattern.

4. The method according to claim 3, wherein the uniformly linear ablation pattern with at least 6 hatching directions is applied at an angle of 40° to 50° per ablation.

5. The method according to claim 4, wherein the uniformly linear ablation pattern with 8 hatching directions is applied at an angle of 45° per ablation.

6. The method according to claim 1, wherein the USP laser (2) for laser etching (A) is operated at a constant wavelength λ in a range between 1020 nm to 1040 nm, as well as at a pulse width ($t_P$) of ≤10 ps.

7. The method according to claim 6, wherein the USP laser (2) for laser etching (A) is operated at a constant wavelength λ of 1030 nm +/−3 nm.

8. The method according to claim 1, wherein at least material-removing steps of cleaning (R) and contrasting (K) are carried out in accordance with a uniformly linear ablation pattern.

9. The method according to claim 8, wherein the uniformly linear ablation pattern with at least 6 hatching directions is applied at an angle of 40° to 50° per ablation.

10. The method according to claim 9, wherein the uniformly linear ablation pattern with 8 hatching directions is applied at an angle of 45° per ablation.

11. A device for performing the multiple step method according to claim 1, at least comprising the USP laser (2) for generating a laser beam (3), a beam deflection unit (4) for moving and focusing the laser beam (3) relative to the surface of the sample (1), a sample clamping unit (5) for positioning the sample (1) relative to the beam deflection unit (4), an electronic control unit (6) for coordinated control of these units in accordance with the method step (G; R; K; A) to be performed.

12. The device according to claim 11, wherein a focus shifter (10) for positioning a laser focus along an optical Z-axis is arranged between the USP laser (2) and the beam deflection unit (4).

13. The device according to claim 12, wherein a beam width unit (11) for increasing a cross section of the laser beam is arranged between the USP laser (2) and the focus shifter (10).

14. The device according to claim 11, wherein the beam deflection unit (4) comprises a dual-axis mirror system (12)

for controlling the laser beam (3) for material processing along the surface of the sample (1) to be processed according to an ablation pattern.

15. The device according to claim 11, wherein the sample clamping unit (5) is configured to position the sample (1) to be processed spatially opposite the beam deflection unit (4) along axes (x, y, z).

* * * * *